United States Patent [19]  
Zoller et al.

[11] Patent Number: 4,785,010  
[45] Date of Patent: Nov. 15, 1988

[54] 2-(AMINOALKYL)-PYRROLE DERIVATIVES, TO TREAT DISORDERS CAUSED BY RESTRICTION IN CEREBRAL FUNCTION

[75] Inventors: Gerhard Zoller, Maintal; Rudi Beyerle, Frankfurt am Main; Ursula Schindler, MöWaldorf; Rolf-Eberhard Nitz, Frankfurt; Piero A. Martorana, Bad Homburg, all of Fed. Rep. of Germany

[73] Assignee: Cassella Aktiengesellschaft, Frankfurt am Main, Fed. Rep. of Germany

[21] Appl. No.: 797,210

[22] Filed: Nov. 12, 1985

Related U.S. Application Data

[62] Division of Ser. No. 604,533, Apr. 27, 1984, abandoned.

[51] Int. Cl.$^4$ .............................................. A61U 31/44
[52] U.S. Cl. .................................................... 514/356

[58] Field of Search ......................................... 514/356

Primary Examiner—Stanley J. Friedman  
Attorney, Agent, or Firm—Perman & Green

[57] ABSTRACT 2-(Aminoalkyl)-pyrrole derivatives of the formula

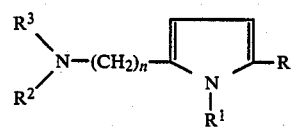

wherein R denotes hydrogen, alkyl or phenyl, $R^1$ denotes, for example, hydrogen, alkyl, alkoxy-carbonyl, aryl, substituted aryl or heteroaryl, $R^2$ and $R^3$ denote, for example, hydrogen, alkyl, alkanoyl, arylcarbonyl, heteroarylcarbonyl or arylenedicarbonyl and n denotes 1, 2 or 3, and their acid addition salts, are used as pharmacological active compounds for combating cerebral aging processes.

12 Claims, No Drawings

2-(AMINOALKYL)-PYRROLE DERIVATIVES, TO TREAT DISORDERS CAUSED BY RESTRICTION IN CEREBRAL FUNCTION

This is a divisional of co-pending application Ser. No. 604,533 filed on Apr. 27, 1984, now abandoned.

The invention relates to new 2-(aminoalkyl)-pyrrole derivatives of the general formula I

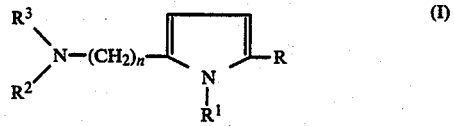

wherein R denotes hydrogen, alkyl($C_1$–$C_5$) or phenyl; $R^1$ denotes hydrogen, alkyl($C_1$–$C_5$), cyano-alkyl($C_1$–$C_4$), alkoxy($C_1$–$C_4$)-carbonyl, alkoxy($C_1$–$C_4$)-carbonyl-alkyl($C_1$–$C_4$), $R^7(R^8)$N-carbonyl-alkyl($C_1$–$C_4$), aryl or aryl-alkyl($C_1$–$C_4$), it being possible for the aryl or the aryl of the aryl-alkyl also to be monosubstituted or polysubstituted by halogen, alkoxy($C_1$–$C_4$), alkyl($C_1$–$C_4$), $R^4(R^5)$N—, hydroxyl, mercapto, alkylmercapto($C_1$–$C_4$), nitro, cyano, alkoxy($C_1$–$C_4$)-carbonyl or alkoxy($C_1$–$C_4$)-carbonyl-alkyl($C_1$–$C_4$), or $R^1$ denotes heteroaryl, heteroaryl-alkyl($C_1$–$C_4$), $R^4(R^5)$N—$R^6$—, hydroxy-carbonyl-alkyl($C_1$–$C_4$), 1-(alkoxy($C_1$–$C_4$)-carbonyl)-2-mercapto-ethyl, 1-(alkoxy($C_1$–$C_4$)-carbonyl)-2-hydroxy-ethyl, 1-(alkoxy($C_1$–$C_4$)-carbonyl)-2-alkoxy($C_1$–$C_4$)-ethyl, 1-(alkoxy($C_1$–$C_4$)-carbonyl)-2-alkylthio($C_1$–$C_4$)-ethyl, 1-(alkoxy($C_1$–$C_4$)-carbonyl)-2-(alkyl($C_1$–$C_4$)-carbonyl-thio)-ethyl, 1-(alkoxy($C_1$–$C_4$)-carbonyl)-2-(alkyl($C_1$–$C_4$)-carbonyl-oxy)-ethyl, 1-(alkoxy($C_1$–$C_4$)-carbonyl)-2-imidazolyl-ethyl, 1-(alkoxy($C_1$–$C_4$)-carbonyl)-2-indolyl-ethyl or 1-(alkoxy($C_1$–$C_4$)-carbonyl)-2-phenyl-ethyl; $R^2$ and $R^3$ independently of one another denote hydrogen, alkyl($C_1$–$C_4$), alkanoyl($C_1$–$C_5$), alkanoyl($C_2$–$C_5$) which is mono-, di- or tri-substituted by amino, alkoxy($C_1$–$C_4$), hydroxyl, alkanoyloxy($C_1$–$C_4$), phenyl or halogen, arylcarbonyl, arylcarbonyl which is mono- or polysubstituted by halogen, alkoxy($C_1$–$C_4$), alkyl($C_1$–$C_4$), amino, $R^4(R^5)$N—, hydroxyl, alkanoyloxy($C_1$–$C_4$), mercapto, alkylmercapto($C_1$–$C_4$), nitro, cyano, alkoxy($C_1$–$C_4$)-carbonyl or amidosulphonyl, or heteroarylcarbonyl, or $R^2$ or $R^3$ together denote vicinal arylenedicarbonyl, vicinal heteroarylene-dicarbonyl, arylene-1-sulphonyl-2-carbonyl, alkylene($C_2$–$C_8$)-dicarbonyl or alkenylene($C_4$–$C_8$)-dicarbonyl, it being possible for the carbon chain of the alkylene- and alkenylene-dicarbonyl also to be interrupted by one or more —O—, —S— or —N($R^4$)— groups, or to contain a spiro-atom, via which a 4-, 5-, 6- or 7-membered ring may be bonded; or $R^2$ and $R^3$ denote cycloalkylcarbonyl with 5 to 7C atoms in the cycloalkyl radical, it also being possible for one —$CH_2$— group to be replaced by —O—, —S— or —N($R^{10}$)—; or (4-chlorophenoxy)-acetyl; or arylene-1-sulphinyl-2-carbonyl or arylene-1-sulphenyl-2-carbonyl; $R^4$ and $R^5$ denote hydrogen or alkyl($C_1$–$C_4$); $R^6$ denotes alkylene($C_1$–$C_4$); $R^7$ and $R^8$ independently of one another denote hydrogen or alkyl($C_1$–$C_4$), or, together with the nitrogen atom to which they are bonded, form a 5- or 6-membered, saturated heterocyclic ring, which may also additionally contain —O— or

$R^9$ denotes hydrogen, alkyl($C_1$–$C_4$), alkoxy($C_1$–$C_4$), phenyl, alkyl($C_1$–$C_4$)-phenyl or alkoxy($C_1$–$C_4$)-phenyl; $R^{10}$ denotes hydrogen or alkanoyl($C_1$–$C_5$); and n denotes 1, 2 or 3; and their acid addition salts, and, in the cases where $R^2$ and $R^3$ together denote 1,2-phenylene-dicarbonyl and at the same time R denotes methyl or ethyl and n denotes the number 1, $R^1$ cannot be ethoxy-carbonylmethyl, ethoxy-carbonyl or o-methoxy-carbonylphenyl, and, in the cases where $R^2$ and $R^3$ together denote 1,2-phenylene-dicarbonyl and at the same time R denotes methyl or ethyl and n denotes the number 2, $R^1$ cannot be ethoxy-carbonyl or ethoxy-carbonylmethyl, and, in the cases where $R^2$ and $R^3$ together denote 1,2-phenylene-dicarbonyl and at the same time n denotes the number 1 and R denotes phenyl, $R^1$ cannot be o-methoxy-carbonylphenyl or ethoxy-carbonylmethyl.

The invention also relates to processes for the preparation of the compounds I and their acid addition salts, and to their use as medicaments.

The alkyl, alkoxy, alkanoyl, alkanoyloxy, alkylene, alkenylene, alkylmercapto and alkoxycarbonyl radicals, including cases where they occur in connection with other radicals, can be straight-chain or branched. The aryl radicals, including cases where they occur in connection with other radicals, in particular denote phenyl or naphthyl, the phenyl radical being preferred. Suitable arylalkyl is, above all, phenethyl and, preferably, benzyl. Arylcarbonyl is preferably benzoyl.

Heteroaryl radicals, including cases where they occur in combination with other radicals, are derived, above all, from 5-membered or 6-membered aromatic heterocyclics, in particular with one or two heteroatoms from the series comprising oxygen, sulphur and nitrogen, for example from furan, thiophene, pyrrole, oxazole, imidazole, thiazole, isoxazole, pyrazole, isothiazole, pyridine, pyrazine, pyridazine and pyrimidine. It is also possible for one or two benzene nuclei to be fused onto these heterocyclics, such as, for example, in the case of benzo(b)thiophene, isobenzofuran, isoindole, quinoline and carbazole. Heteroaryl-alkyl radicals are preferably heteroaryl-methyl radicals. Halogen is, above all, fluorine, chlorine or bromine. Vicinal arylene-dicarbonyl is understood as meaning those aryl radicals which are derived from aromatic 1,2-dicarboxylic acids, for example phthaloyl. Alkylene-dicarbonyl is, in particular, alkylene-1,2-, -1,3- or 1,4-dicarbonyl, preferably succinyl. Alkenylene-di-carbonyl is, in particular, alkenylene-1,2-, -1,3- or -1,4-carbonyl, for example citraconoyl, but preferably maleoyl.

Examples of alkyl radicals R are methyl, ethyl and isopropyl. Methyl is preferred for the substituent R. Examples of substituents which can be represented by $R^1$ are: hydrogen, methyl, ethyl, propyl, isopropyl, but-1-yl, but-2-yl, isobutyl, tert.-butyl, isopentyl, aminomethyl, 2-aminoethyl, 3-amino-n-propyl, 2-(N,N-dimethylamino)-ethyl, 2-(N,N-diethylamino)-ethyl, cyanomethyl, 2-cyanoethyl, 3-cyano-propyl, methoxy-carbonyl, n-propoxy-carbonyl, i-propoxy-carbonyl, n-butoxy-carbonyl, t-butoxy-carbonyl, methoxycarbonyl-methyl, n-propoxycarbonylmethyl, i-butoxycarbonylmethyl, 2-(methoxycarbonyl)-ethyl, 2-(ethoxycarbonyl)-ethyl, 2-(i-propoxycarbonyl)-ethyl, 2-(methoxycarbonyl)-propyl, 2-(ethoxycarbonyl)-propyl, aminocarbonylmethyl, 2-(aminocarbonyl)-ethyl, N,N-dimethylaminocarbonylmethyl, (N,N-dimethylaminoethyl)-aminocarbonyl-methyl, ethylaminocarbonylethyl, morpholinocarbonylmethyl, 4-methylpiperazin-1-yl-carbonylmethyl, 4-phenylpiperazin-1-yl-carbonylmethyl, 4-(o-, m- or p-methoxyphenyl)-piperazin-1-yl-carbonylmethyl, pyrrolidinocarbonyl-methyl, N,N-dimethylaminocarbonyl-ethyl, 2-(4-methylpiperazin-1-ylcarbonyl)-ethyl, phenyl, 2-methylphenyl, 3-methylphenyl, 4-methylphenyl, 2-methoxyphenyl, 3-methoxyphenyl, 4-methoxyphenyl, 3,4-dimethoxyphenyl, o-, m- or p-chlorophenyl, 4-dimethylaminophenyl, 4-mercaptophenyl, 4-methoxybenzyl, 2-thienylmethyl, 2-furylmethyl, 2-, 3- or 4-pyridylmethyl, 2-, 3- or 4-pyridyl, 1-(methoxy-carbonyl)-2-mercapto-ethyl, 1-(ethoxy-carbonyl)-2-phenyl-ethyl, 1-(i-butoxy-carbonyl)-2-(3-indolyl)-ethyl, 1-(propoxy-carbonyl)-2-hydroxy-ethyl, 1-(methoxy-carbonyl)-2-hydroxy-ethyl, 1-(methoxy-carbonyl)-2-methoxy-ethyl, 1-(methoxy-carbonyl)-2-butoxy-ethyl, 1-(i-butoxy-carbonyl)-2-ethoxy-ethyl, 1-(ethoxy-carbonyl)-2-(methylthio)-ethyl, 1-(propoxy-carbonyl)-2-(propylthio)-ethyl, 1-(ethoxy-carbonyl)-2-(acetylthio)-ethyl, 1-(methoxy-carbonyl)-2-(formyl-thio)-ethyl, 1-(ethoxy-carbonyl)-2-(acetoxy)-ethyl, 1-(methoxy-carbonyl)-2-(formyloxy)-ethyl, 1-(ethoxycarbonyl)-2-(4- or 5-imidazolyl)-ethyl, 1-(propoxy-carbonyl)-2-(3-indolyl)-ethyl and 1-(methoxy-carbonyl)-2-phenyl-ethyl.

Preferred radicals for the substituent $R^1$ are: hydrogen, $R^4R^5N$—$R^6$—, benzyl or phenethyl, it being possible for the phenyl group in the benzyl or phenethyl radical also to be substituted by one, two or three methyl and/or methoxy groups, phenyl, which can also be mono-, di- or tri-substituted by alkoxy-($C_1$-$C_4$)-carbonyl, alkyl($C_1$-$C_4$), halogen, alkoxy($C_1$-$C_4$) and hydroxyl, methoxy-carbonyl-phenyl, methoxy-carbonyl-dimethoxyphenyl, methoxy-carbonyl-trimethoxyphenyl, imidazolylethyl, cyanoethyl, methoxycarbonylmethyl and acetaminoethyl. Examples of preferred radicals $R^1$ are: hydrogen, dimethoxyphenyl-ethyl, in particular 3,4-dimethoxy-phenyl-ethyl, methoxycarbonylmethyl, imidazolylethyl, in particular 2-(4-imidazolyl)-ethyl, 3-(1-imidazolyl)-propyl, acetaminoethyl, (methoxy-carbonyl)-dimethoxy-phenyl, in particular 2-(methoxy-carbonyl)-4,5-dimethoxy-phenyl, 2-(dimethylamino)-ethyl, aminocarbonylmethyl, 2-cyanoethyl, 2-methoxy-carbonyl-phenyl, 2-methoxy-carbonyl-4,5,6-trimethoxy-phenyl and 2-methoxy-carbonyl-4,5-dimethoxyphenyl.

Heterocyclic radicals in the 1-(alkoxy($C_1$-$C_4$)-carbonyl)-2-imidazolyl-ethyl and 1-(alkoxy($C_1$-$C_4$)-carbonyl)-2-indolylethyl radicals represented by $R^1$ are, in particular, 4- or 5-imidazolyl and 3-indolyl radicals.

$R^2$ and $R^3$ can also independently of one another represent, for example: hydrogen, methyl, ethyl, propyl, isopropyl, but-1-yl, but-2-yl, isobutyl, isopentyl, pentyl, formyl, acetyl, propionyl, butyryl, isobutyryl, valeryl, isovaleryl, pivaloyl, chloroacetyl, aminoacetyl, methoxyacetyl, dichloroacetyl, trichloroacetyl, 3-methoxypropyl-carbonyl, benzoyl, o-, m- or p-methyl-benzoyl, dimethylbenzoyl, o-, m- or p-methoxybenzoyl, dimethoxybenzoyl, 3,4-dimethoxybenzoyl, o-, m- or p-chlorobenzoyl, o-, m- or p-bromobenzoyl, o-, m- or p-aminobenzoyl, o-, m- or p-hydroxybenzoyl, 4-hydroxy-3-methoxy-benzoyl, 4-acetoxy-3-methoxybenzoyl, 2-phenyl-2-hydroxyacetyl (mandeloyl), 2-phenyl-2-acetoxy-acetyl, 2-phenyl-3-hydroxy-propionyl (tropoyl), 2-phenyl-3-acetoxy-propionyl, 2-, 3- or 4-pyridyl-carbonyl, 2-thienylcarbonyl or 2-furylcarbonyl.

Further examples of $R^2$ and/or $R^3$ are: cyclopentylcarbonyl, cyclohexyl-carbonyl, cycloheptyl-carbonyl, pyrrolidin-2-yl-carbonyl, 1-formyl-pyrrolidin-2-yl-carbonyl, 1-acetyl-pyrrolidin-2-yl-carbonyl, pyrrolidin-3-yl-carbonyl, piperidin-2-yl-carbonyl, piperidin-3-yl-carbonyl, piperidin-4-yl-carbonyl, 4-chlorophenoxy-acetyl, 2-, 3- or 4-nitrobenzoyl, 2-, 3- or 4-cyanobenzoyl, 2-, 3- or 4-alkoxy($C_1$-$C_4$)-carbonyl-benzoyl, such as, for example, 2-, 3- or 4-methoxy-carbonyl-benzoyl, 2-, 3- or 4-ethoxy-carbonyl-benzoyl, 2-, 3- or 4-propoxy-carbonyl-benzoyl and 2-, 3- or 4-sec.-butoxy-carbonyl-benzoyl.

Examples of $R^2$ and $R^3$ together are: phthaloyl-dicarbonyl, pyridyl-2,3-dicarbonyl, succinyl, glutaryl, maleoyl, citraconoyl, butene-1,4-dicarbonyl, phenyl-1-sulphonyl-2-carbonyl, 2-thiabutanedioyl (—CO—S—CH$_2$—CO—) and 2,2-tetramethylenepropane-1,3-dicarbonyl. Preferred radicals for $R^2/R^3$ are, for example: H/H, nicotinoyl/H, 3,4-dimethoxybenzoyl/H, acetamino/H, phenylene-1-sulphonyl-2-carbonyl, phthaloyl, phenylene-1-sulphenyl-2-carbonyl and phenylene-1-sulphinyl-2-carbonyl.

The cycloalkylcarbonyl radical represented by $R^2$ and/or $R^3$, including cases where a —CH$_2$— group is replaced by —O—, —S— or —N($R^{10}$)—, preferably contains 5C atoms in the cycloalkyl radical.

Preferred compounds of the formula I are those in which R denotes a methyl radical and/or in which $R^2$ denotes hydrogen or represents a radical together with the radical $R^3$.

The 2-(aminoalkyl)-pyrrole derivatives of the formula I are prepared in a manner which is known per se by reacting a 1,4-diketone of the formula II with an amine of the formula III

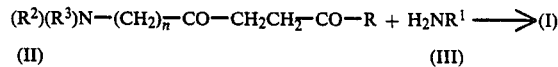

$$(R^2)(R^3)N-(CH_2)_n-CO-CH_2CH_2-CO-R + H_2NR^1 \longrightarrow (I)$$
$$(II) \hspace{3cm} (III)$$

in a suitable inert solvent or solvent mixture at temperatures from 0° to 200° C. In the compounds II and III, the radicals R, $R^1$, $R^2$ and $R^3$ and n have the meanings already given.

Temperatures of 20° to 100° C. are adequate in many cases. Examples of suitable solvents are alcohols, in particular those with 1 to 6C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8C atoms in the molecule, such as, for example, diethyl ether, methyl ethyl ether, di-n-propyl ether, diisopropyl ether, methyl n-butyl ether, ethyl propyl ether, dibutyl ether, tetrahydrofuran, 1,4-dioxane, 1,2-dimethoxyethane and bis-$\beta$-methoxyethyl ether; polyethers, such as, for example, polyethylene glycols with a molecular weight of up to about 600; oligoethylene glycol dimethyl ethers, such as, for example, pentaglyme; aliphatic carboxylic acids, in particular formic acid and acetic acid; glycols and partially etherified glycols, such as, for example, ethylene glycol, propylene glycol, trimethylene glycol, ethylene glycol monomethyl ether, ethylene glycol monoethyl ether and diethylene glycol monoethyl ether; ketones, in particular those with 3 to 10C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-isobutyl ketone, cyclopentanone, cyclohexanone, benzophenone and acetophenone; aliphatic hydrocarbons, such as, for example, low-boiling and high-boiling petroleum ethers; aromatic hydrocarbons, such as, for example, benzene, toluene and o-, m- and p-xylene; halogenated aliphatic or aromatic hydrocarbons, such as, for example, methylene chloride, chloroform, carbon tetrachloride, chlorobenzene and dichlorobenzene; nitriles, such as, for example, acetonitrile; amides, such as, for example, dimethylformamide and N-methyl-pyrrolidone; hexamethylphosphoric acid triamide; sulphoxides, such as, for example, dimethylsulphoxide; and water. Mixtures of different solvents can also be used.

The starting components are usually employed in approximately equimolar amounts in the preparation of the compounds of the formula I. The amine III can also be used in the form of an acid addition salt. The batches are worked up by customary methods. If appropriate, the reaction can also be carried out in the presence of a base or a base mixture. Examples of suitable bases are tertiary aliphatic amines, such as, for example, triethylamine, tri-n-propylamine and tri-iso-propylamine, and furthermore pyridine, as well as alkali metal carbonates, bicarbonates, formates and acetates.

The amines of the formula III required as starting substances are known, or they can easily be prepared by the customary methods for the preparation of primary amines. The 1,4-diketones of the formula II required as starting substances can easily be prepared, where these are not already known, by catalysed addition of an aldehyde of the formula IV onto a vinylcarbonyl compound of the formula V

(IV)    (V)

in accordance with the process of H. Stetter, Angew. Chem. 88 (1976), 695 to 704, the radicals R, $R^2$ and $R^3$ and n in the compounds IV and V having the meanings already given. Cyanide ions in the form of alkali metal cyanides or thiazolium salts, such as 5-(2-hydroxyethyl)-3-benzyl-4-methyl-1,3-thiazolium chloride, or other azolium salts in the presence of a base, such as triethylamine or sodium acetate, are mentioned as suitable catalysts in this process. The reaction is carried out with or without a solvent at temperatures from 0° C. to the reflux temperature of the solvent used. It may be appropriate to use the aldehyde of the formula IV in the form of its hydrate.

Aldehydes of the formula IV can easily be obtained by acylation of aminoacetaldehyde acetals with carboxylic acid derivatives, the carboxylic acid derivatives used being, in particular, carboxylic acids, carboxylic acid esters, carboxylic acid anhydrides and carboxylic acid chlorides. The reactions are carried out in a manner which is known per se, if necessary with the aid of suitable catalysts. On the other hand, the compounds of the formula IV are also accessible by alkylation of suitably substituted amines, amides or imides by processes which are known from the literature.

The substituents $R^2$ and $R^3$ can be split off from compounds of the formula I according to the invention and replaced by hydrogen by processes which are known from the literature. This splitting-off is particularly easy if the substituents $R^2$ and $R^3$ are acyl radicals, in particular, 1,2-arylene-dicarbonyl, alkylenedicarbonyl or alkenylenedicarbonyl. In these cases, the splitting-off can usually be carried out by boiling with hydrazine or hydrazine hydrate. Compounds of the formula I according to the invention in which $R^2$ and $R^3$ and, if appropriate, also $R^1$ denote hydrogen are thus obtained. The compounds thus obtained can be converted into other compounds of the formula I according to the invention by acylation and/or alkylation by known methods. It is advantageous to match the sequence of the individual reaction steps to the required circumstances.

If $R^2$ and $R^3$ together denote arylene-1-sulphinyl-2-carbonyl or arylene-1-sulphonyl-2-carbonyl, the compounds can also be prepared by oxidation of the corresponding arylene-1-sulphenyl-2-carbonyl or arylene-1-sulphinyl-2-carbonyl compounds by processes which are known from the literature.

The compounds of the formula I can advantageously also be prepared by replacing the 1,4-diketone of the formula II in the abovementioned preparation process by a 1,4-diketal of the formula IIa:

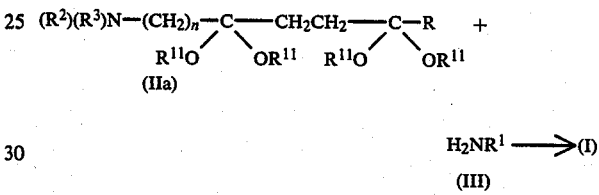

wherein $R^{11}$ denotes alkyl, for example with 1 to 6C atoms, and two adjacent radicals $R^{11}$ together also denote alkylene, for example with 2 to 3C atoms.

The reaction conditions are the same as those for the reaction of the compounds II with the amines III.

The educts of the formula IIa are obtained from aminoketals of the formula VI by reaction with acid derivatives AcX of the formula VII, which introduce the radical $R^2CO-$, $R^3CO-$ or the vicinal arylene-, heteroarylene-, alkylene- or alkenylenedicarbonyl radicals represented by $R^2$ and $R^3$ together, or the arylene-1-sulphenyl- or -sulphinyl- or -sulphonyl-2-carbonyl radicals represented by $R^2$ and $R^3$ together:

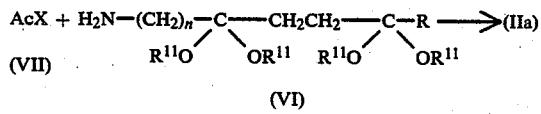

Accordingly, in the formula VII, the radical Ac has the meaning of the abovementioned radicals and AcX represents an acid halide, in particular acid chloride, acid anhydride, mixed sulphonic acid/carboxylic acid halide or anhydride or another activated acid derivative. The reaction can be carried out at room temperature or elevated temperature, advantageously in a suitable solvent, for example an ether, such as, for example, tetrahydrofuran, dioxane, ethylene glycol dimethyl ether, diethyl ether or dipropyl ether, dimethylformamide, dimethylsulphoxide and the like, if appropriate in the presence of bases, such as, for example, pyridine, triethylamine, potassium carbonate, sodium carbonate and the like.

The aminoketals of the formula VI are formed from readily accessible compounds of the formula IIa in which $R^2$ and $R^3$ together denote phthaloyl, by splitting off the phthalic acid radical with hydrazine in inert solvents, such as alcohols, aromatics, ethers, diols, cyclic ethers or aprotic solvents, such as dimethylformamide or dimethylsulphoxide, at temperatures between room temperature and the boiling point of the solvent.

The compounds of the formula IIa in which $R^2$ and $R^3$ together denote phthaloyl (=phenylene-1,2-dicarbonyl) are formed from compounds of the formula II by methods which have been known for a long time in the literature for the synthesis of ketals (compare Houben-Weyl "Methoden der Org. Chemie" ("Methods of Organic Chemistry"), Volume VI/3, (1965), pages 217 et seq.; Volume VII/2b, (1976), pages 1886 et seq.). The dimethyl and ethylene glycol ketals, for example, have proved particularly suitable.

Compounds of the formula IIa in which $R^2$ or $R^3$ does not represent acyl radicals but alkyl radicals can be prepared, for example, from the compounds of the formula VI by reductive amination by processes which are known per se (compare, for example, Houben-Weyl "Methoden der Org. Chemie" ("Methods of Organic Chemistry"), Volume 11/1 (1958), pages 641 et seq.).

If the 2-(aminoalkyl)-pyrrole derivatives of the formula I contain basic radicals, they form acid addition salts with inorganic or organic acids. Inorganic and organic acids are suitable for the formation of such acid addition salts. Examples of suitable acids are: hydrogen chloride, hydrogen bromide, naphthalenedisulphonic acids, in particular naphthalene-1,5-disulphonic acid, phosphoric acid, nitric acid, sulphuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulphamic acid, phenylpropionic acid, gluconic acid, ascorbic acid, nicotinic acid, isonicotinic acid, methanesulphonic acid, p-toluenesulphonic acid, citric acid and adipic acid. Pharmacologically acceptable acid addition salts are preferred. The acid addition salts are prepared in the customary manner by combining the components, advantageously in a suitable solvent or diluent. In the synthesis of the compounds of the formula I, the acid addition salts may first be obtained in the course of working up. If desired, the free compounds of the general formula I can be obtained from the acid addition salts in a known manner, for example by dissolving or suspending in water, rendering the solution alkaline, for example with sodium hydroxide solution, and subsequent isolation.

The compounds of the formula I according to the invention and their pharmacologically acceptable acid addition salts have useful pharmacological properties.

The aminoalkylpyrroles of the formula I according to the invention and their pharmacologically acceptable salts have an action on the central nervous system, for example they exhibit nootropic actions, and are used for the treatment of disorders which are characterised by a restriction in cerebral function, in particular memory performance, and for reducing cerebral ageing processes. Surprisingly, they are considerably superior to the compounds known hitherto which have the same type of action. They exhibit an excellent activity in various tests, such as, for example, in the prolonging of the survival time, under sodium nitrite hypoxia in accordance with the method of Gibsen and Bless (J. Neurochemistry 27, (1976)), and in the improvement of nitrogen-induced hypoxia tolerance, in which experimental animals are respirated with pure nitrogen, after premedication with the products investigated, and the lengthening of the period between the start of respiration and electrical neutrality of the electroencephalogram and the lethality are measured.

The products according to the invention also have a very good action in tests aimed directly at ascertaining the learning and memory performance, such as, for example, the known "avoidance" tests.

Investigation by the above tests and a number of other tests, such as, for example, the gamma-butyrolactone test, shows that, surprisingly, the compounds according to the invention have a particularly advantageous action profile at low doses, which is not present in known products in this form, coupled with a low toxicity.

The compounds of the formula I and their physiologically acceptable salts thus represent an enrichment of pharmacy.

It has furthermore been found that the compounds of the present formula I which are already known as intermediates from the literature reference H. Stetter and P. Lappe, Liebigs Ann. Chem. 1980, 703 to 714, in which $R^2$ and $R^3$ together denote 1,2-phenylene-dicarbonyl and at the same time R denotes methyl or ethyl, n denotes the number 1 and $R^1$ denotes ethoxy-carbonyl-methyl, ethoxy-carbonyl or o-methoxy-carbonyl-phenyl, or in which $R^2$ and $R^3$ together denote, 1,2-phenylene-dicarbonyl and at the same time R denotes methyl or ethyl, n denotes the number 2 and $R^1$ denotes ethoxy-carbonyl or ethoxy-carbonyl-methyl, or in which $R^2$ and $R^3$ together denote 1,2-phenylene-dicarbonyl and at the same time n denotes the number 1, R denotes phenyl and $R^1$ denotes o-methoxy-carbonyl-phenyl or ethoxy-carbonyl-methyl, have the same pharmacological properties affecting the central nervous system, although to a smaller extent. The compounds of the formula I according to the invention and their pharmacologically acceptable acid addition salts and the abovementioned compounds can therefore be used on humans as medicines, for example for combating or preventing disorders which are caused by a restriction of the cerebral function and for the treatment and prophylaxis of cerebral aging processes.

The compounds of the formula I and the abovementioned compounds and their pharmacologically acceptable acid addition salts can be administered as medicines themselves, as mixtures with one another or in the form of pharmaceutical formulations which permit enteral or parenteral use and contain, as the active constituent, an effective dose of at least one compound of the formula I or one abovementioned compound or one acid addition salt thereof, in addition to customary pharmaceutically acceptable excipients and additives. The formulations usually contain about 0.5 to 90 percent by weight of the therapeutically active compound.

The medicines can be administered orally, for example in the form of pills, tablets, lacquered tablets, coated tablets, granules, hard and soft gelatin capsules, solutions, syrups, emulsions or suspensions or aerosol mixtures. However, the administration can also be rectal, for example in the form of suppositories, or parenteral, for example in the form of injection solutions, or percutaneous, for example in the form of ointments or tinctures.

The pharmaceutical products are prepared in a manner which is known per se, pharmaceutically inert inorganic or organic excipients being used. Pills, tablets, coated tablets and hard gelatin capsules can be prepared, for example using lactose, maize starch or derivatives theeof, talc, stearic acid or salts thereof and the like. Examples of excipients for soft gelatin capsules and suppositories are fats, waxes, semi-solid and liquid polyols, natural or hard oils and the like. Suitable excipients for the preparation of solutions and syrups are, for example, water, sucrose, invert sugar, glucose, polyols and the like. Examples of suitable excipients for the preparation of injection solutions are water alcohols, glycerol, polyols, vegetable oils and the like.

Besides the active compounds and excipients, the pharmaceutical products can also contain additives, such as, for example, fillers, extenders, disintegrating agents, binders, lubricants, wetting agents, stabilisers, emulsifiers, preservatives, sweeteners, colorants, flavouring agents, aromatising agents, thickeners, diluents and buffer substances, as well as solvents or solubilising agents or agents for achieving a depot effect, and salts for modifying the osmotic pressure, coating agents or antioxidants. They can also contain two or more compounds of the formula I or their pharmacologically acceptable acid addition salts, and furthermore one or more other therapeutically active substances.

Examples of such other therapeutically active substances are agents which stimulate blood flow, such as dihydroergocrystine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronar dilators, such as carbocromene, dipyridamole, nifedipine and perhexiline, anti-anginal compounds, such as isosorbide dinitrate, isosorbide mononitrate, glycerol nitrate, molsidomine and verapamil, and β-blockers, such as propranolol, oxprenolol, atenolol, metoprolol and penbutolol. The compounds can furthermore be combined with other substances having a nootropic action, such as, for example, piracetam, or substances having an action on the central nervous system, such as pirlindol, sulpride and the like.

The dosage can vary within wide limits and is to be adapted to the individual circumstances in each particular case. In general, a daily dose of about 0.1 to 1 mg/kg, preferably 0.3 to 0.5 mg/kg, of body weight is general appropriate to achieve effective results with oral administration, and with intravenous administration the daily dose is in general about 0.01 to 0.3 mg/kg, preferably 0.05 to 0.1 mg/kg, of body weight. The daily dose is usually divided into several, for example 2, 3 or 4, part administrations, especially where relatively large amounts are administered. If appropriate, it may be necessary, depending on the individual circumstances, to deviate upwards or downwards from the stated daily dose. Pharmaceutical products usually contain 0.1 to 50 mg, preferably 0.5 to 10 mg, of active compound of the formula I or of the compounds mentioned or of a pharmacologically acceptable salt per dose.

1-(Ethoxy-carbonyl- or ethoxy-carbonylmethyl- or o-mehoxy-carbonyl-phenyl)-2-(phthalimido-methyl)-5-methyl- or -ethyl-pyrroles are known from the literature reference H. Stetter and P. Lappe, Liebigs Ann. Chem., 1980, 703–714, as intermediates for the preparation of bicyclic and tricyclic pyrrole systems. However this literature reference gives no indication that the compounds have useful pharmacological properties.

EXAMPLE 1

1-(2-Dimethylamino-ethyl)-2-(phthalimido-methyl)-5-methyl-pyrrole 7.8 g (0.03 mol) of 6-phthalimido-2,5-hexanedione (compare Example 2) and 2.7 g (0.03 mol) of N,N-dimethylaminoethylamine are stirred in 150 ml of acetic acid at 80° C. for 3 hours. After concentration of the mixture, the residue is taken up in aqueous sodium bicarbonate solution, the mixture is extracted with methylene chloride, the extract is dried and concentrated and the residue is recrystallised from methanol.

Yield: 6.5 g, 70% of theory; melting point: 125° to 126° C.

Analysis: Calculated: C 69.4, H 6.8, N 13.5, O 10.3; Found: C 69.1, H 6.6, N 13.6, O 10.6.

EXAMPLE 2

(a) The starting product 6-phthalimido-2,5-hexanedione required in Example 1 can be prepared as follows: 66 g (0.32 mol) of phthalimido-acetaldehyde hydrate (compare Example 3), 70.1 g (1.0 mol) of methyl vinyl ketone, 31.5 g of 3-benzyl-5-(2-hydroxy-ethyl)-4-methyl-1,3-thiazolium chloride and 155 ml of triethylamine are heated under reflux in 600 ml of ethanol for 16 hours. After the mixture has been concentrated, the residue is taken up in aqueous sodium bicarbonate solution, the mixture is extracted with methylene chloride, the extract is filtered over active charcoal and concentrated and the residue is recrystallised from methanol.

Yield: 55.1 g, 67% of theory; melting point: 117° to 119° C.

Analysis: Calculated: C 64.9, H 5.1, N 5.4, O 24.7; Found: CC 64.8, H 5.4, N 5.5, O 24.7.

The following compounds can be prepared, for example, in a similar manner:

(b) 6-Succinimido-hexane-2,5-dione, (c) 6-maleimido-hexane-2,5-dione, (d) 6-acetamido-hexane-2,5-dione, (e) 6-(N,N-dimethylamino)hexane-2,5-dione, (f) 6-benzamido-hexane-2,5-dione, (g) 6-(4-methylbenzamido)-hexane-2,5-dione, (h) 6-(4-chlorobenzamido)hexane-2,5-dione, (i) 6-(4-methoxybenzamido)-hexane-2,5-dione, (j) 6-(3,4-dimethoxybenzamido)-hexane-2,5-dione, (k) 6-(thiophene-2-carboxamido)-hexane-2,5-dione, (1) 6-(nictoinamdio)-hexane-2,5-dione, (m)6-(pyridine-2,3-dicarboximido)-hexane-2,5-dione and (n) 6-(o-sulphobenzoic acid imido)-hexane-2,5-dione.

EXAMPLE 3

The starting substance phthalimido-acetaldehyde hydrate required in Example 2 can be prepared in accordance with the teachings of Federal German Pat. No. 982,711 as follows:

(a) 500 g of acetamide are melted in an oil bath. After addition of 243.5 g (1.31 mol) of potassium phthalimide, the mixture is warmed to 130° C. and 259 g (1.31 mol) of bromoacetaldehyde diethyl acetal are added at this temperature. When the addition has ended, the mixture is warmed to 170° C. for 30 minutes and cooled, 1 liter of water is added and the mixture is stirred overnight. The solid which has precipitated is filtered off with suctionn and extracted by stirring with methylene chloride and the methylene chloride phase is dried and concentrated.

Yield: 256.6 g of phthalimido-acetaldehyde diethyl acetal=74% of theory, melting point: 70° to 71° C.

256.6 g (0.975 mol) of phthalimido-acetaldehyde diethyl acetal, 270 ml of formic acid, 25 ml of concentrated hydrochloric acid and 40 ml of water are warmed at 100° C. for 10 minutes and, after cooling, diluted with 3 liters of water, concentrated to 2 liters of solution and cooled. The product which has precipitated is filtered off with suction and dried.

Yield: 162 g=80% of theory of phthalimido-acetaldehyde hydrate of melting point: 112° to 113° C.

Instead of bromoacetaldehyde diethyl acetal, it is also possible to use chloroacetaldehyde diethyl acetal in the above process with equally good success.

(b) 100 g (0.54 mol) of potassium phthalimide, 90 g (0.46 mol) of bromoacetaldehyde diethyl acetal and 1 g of potassium iodide are stirred in 800 ml of dimethylformamide at 100° C. for 66 hours. After the mixture has been concentrated to 100 ml, 200 ml of water are added, the product is filtered off with suction, 145 ml of formic acid, 20 ml of water and 15 ml of concentrated hydrochloric acid are added, the mixture is heated at 100° C. for 10 minutes, 1 liter of water is added, the mixture is filtered over active charcoal and cooled and the product is filtered off with suction and dried.

Yield: 62.4 g=66% of theory of phthalimido-acetaldehyde hydrate of melting point: 111° to 113° C.

The following compounds, for example, can be prepared in an analogous manner by processes (a) and (b):

Pyridine-2,3-dicarboximido-acetaldehyde and -acetaldehyde diethyl acetal, succinimido-acetaldehyde diethyl acetal, succinimido-acetaldehyde, maleimido-acetaldehyde diethyl acetal, maleimido-acetaldehyde and (1,2-benzisothiazole 1,1-dioxide-3(2H)-on-2-yl)-acetaldehyde and -acetaldehyde diethyl acetal (=o-sulphobenzoic acid imido-acetaldehyde and o-sulphobenzoic acid imido-acetaldehyde acetal).

EXAMPLE 4

1-(2-(3,4-Dimethoxyphenyl)-ethyl)-2-(phthalimido-methyl)-5-methyl-pyrrole 13.0 g (0.05 mol) of 6-phthalimido-2,5-hexanedione and 9.1 g (0.05 mol) of 2-(3,4-dimethoxyphenyl)-ethylamine are stirred in 250 ml of acetic acid at 80° C. for 7 hours. After working up as in Example 1, 7.3 g of product are obtained.

Yield: 36% of theory; melting point: 112° to 113° C.

Analysis: Calculated: C 71.3, H 6.0, N 6.9, O 15.8; Found: C 70.9, H 6.0, N 6.8, O 16.1.

EXAMPLE 5

1-(Methoxycarbonyl-methyl)-2-(phthalimido-methyl)-5-methylpyrrole 18.1 g (0.07 mol) of 6-phthalimido-2,5-hexanedione, 10.0 g (0.08 mol) of glycine methyl ester hydrochloride and 6.6 g (0.08 mol) of sodium acetate are stirred in 300 ml of acetic at 80° C. for 3 hours. After the mixture has been concentrated, the residue is taken up in aqueous sodium bicarbonate solution, the mixture is extracted with methylene chloride, the extract is dried and concentrated and the residue is recrystallised from methanol.

Yield: 14.5 g, 66% of theory, melting point: 134° C.

Analysis: Calculated: C 65.4, H 5.2, N 9.0, O 20.5; Found: C 65.1 , H 5.1, N 9.0, O 20.8.

EXAMPLE 6

1-(2-Methoxy-carbonyl-4,5-dimethoxy-phenyl)-2-(phthalimidomethyl)-5-methyl-pyrrole 13.0 g (0.05 mol) of 6-phthalimido-2,5-hexanedione and 10.6 g (0.05 mol) of methyl 2-amino-4,5-dimethoxybenzoate are stirred in 250 ml of acetic acid at 100° C. for 30 hours and the mixture is worked up as in Example 1.

Yield: 10.3 g, 47% of theory, melting point: 184° to 185° C.

Analysis: Calculated: C 66.4, H 5.1, N 6.4, O 22.1; Found: C 66.4, H 5.0, N 6.6, O 22.5.

EXAMPLE 7

2-(Phthalimido-methyl)-5-methyl-pyrrole 36.3 g (0.14 mol) of 6-phthalimido-2,5-hexanedione, 54 g (0.7 mol) of ammonium acetate and 1 g of ammonium chloride are stirred in 700 ml of acetic acid at 80° C. for 1 hour and the mixture is worked up as in Example 1.

Yield: 32.2 g, 96% of theory, melting point: 173° to 174° C.

Analysis: Calculated: C 70.0, H 5.0, N 11.7, O 13.3; Found: C 69.7, H 5.3, N 11.4, O 13.8.

EXAMPLE 8

1-(2-(Imidazol-4- or -5-yl)-ethyl)-2-(phthalimido-methyl)-5-methyl-pyrrole hydrochloride 5.2 g (0.02 mol) of 6-phthalimido-2,5-hexanedione, 3.7 g (0.02 mol) of histamine dihydrochloride and 3.4 g (0.04 mol) of sodium acetate are stirred in 70 ml of acetic acid at 80° C. for 3 hours. After working up as in Example 1, ethanolic hydrochloric acid is added and the product is filtered off and dried.

Yield: 4.0 g, 54% of theory, melting point: 218° to 219° C.

Analysis:
Calculated: C 61.5, H 5.2, N 15.1, O 8.6, Cl 9.6; Found: C 61.2, H 5.3, N 14.8, O 9.0, Cl 9.4.

EXAMPLE 9

1-(Methoxycarbonyl-methyl)-2-(phthalimido-methyl)-5-methylpyrrole 11.4 g (0.044 mol) of 6-phthalimido-2,5-hexanedione, 27.6 g ((0.22 mol) of glycine methyl ester hydrochloride and 9.1 g (0.11 mol) of sodium acetate are heated under reflux in ethanol for 16 hours and the mixture is worked up as in Example 1.

Yield: 6.1 g, 44% of theory, melting point: 134° to 135° C.

Analysis: Calculated: C 65.4, H 5.2, N 9.0, O 20.5; Found: C 65.7, H 5.2, N 9.0, O 20.1.

EXAMPLE 10

1-(2-Acetylamino-ethyl)-2-(phthalimido-methyl)-5-methyl-pyrrole 4.6 g (0.018 mol) of 6-phthalimido-2,5-hexanedione and 1.8 g (0.018 mol) of 2-(acetylamino)-ethylamine are stirred in 120 ml of acetic acid at 80° C. for 4 hours. Working up is carried out as described in Example 1:

Yield: 1.5 g, 26% of theory, melting point: 191° to 192° C.

Analysis: Calculated: C 66.4, H 5.9, N 13.2, O 14.8; Found: C 66.2, H 6.0, N 12.9, O 14.9.

EXAMPLE 11

2-(Amino-methyl)-5-methyl-pyrrole 60.9 g (0.23 mol) of 2-(phthalimido-methyl)-5-methyl-pyrrole (compare Example 7) and 114 ml (2.3 mol) of hydrazine hydrate are heated under reflux in 1 liter of ethanol for 15 minutes. After the mixture has been cooled, it is filtered with suction, the filtrate is concentrated, the residue is taken up in methylene chloride, the mixture is filtered, the filtrate is concentrated and the residue is recrystallised from toluene.

Yield: 23.1 g, 91% of theory.

EXAMPLE 12

1-(2-(3,4-Dimethoxyphenyl)-ethyl)-2-(amino-methyl)-5-methylpyrrole 6.0 g (0.015 mol) of 1-(2-(3,4-dimethoxyphenyl)-ethyl)-2-(phthalimido-methyl)-5-methyl-pyrrole (compare Example 4) and 7 ml (0.15 mol) of hydrazine hydrate are heated under reflux for 30 minutes. After the mixture has been concentrated, the residue is taken up in methylene chloride, the mixture is filtered, the filtrate is concentrated and the residue is chromatographed over a silica gel column.

Yield: 3.0 g, 74% of theory.

EXAMPLE 13

1-(2-(Dimethylamino-ethyl)-2-(amino-methyl)-5-methyl-pyrrole 5.0 g (0.014 mol) of 1-(2-dimethylamino-ethyl)-2-(phthalimidomethyl)-5-methyl-pyrrole (compare Example 1) and 7 ml (0.15 mol) of hydrazine hydrate are heated under reflux for 30 minutes. After the mixture has been cooled, the phthalic acid hydrazide is filtered off with suction, the filtrate is concentrated, the residue is taken up in methylene chloride, the mixture is filtered again and the filtrate is concentrated.

Yield: 2.4 g, 94% of theory.

Analysis: Calculated: C 66.3, H 10.6, N 23.2; Found: C 66.5, H 10.1, N 22.8.

EXAMPLE 14

1-(2-Dimethylamino-ethyl)-2-(3,4-dimethoxy-benzoylamino-methyl-5-methyl-pyrrole 2.3 g (0.013 mol) of 3,4-dimethoxybenzoic acid are heated under reflux with 2.1 g (0.013 mol) of carbonyl diimidazole in 40 ml of tetrahydrofuran for 15 minutes. After addition of 2.3 g (0.013 mol) of 1-(2-(dimethylamino)-ethyl)-2-(aminomethyl)-5-methyl-pyrrole (compare Example 12), the mixture is stirred at room temperature for 3 hours and concentrated, aqueous sodium bicarbonate solution is added, the mixture is extracted with methylene chloride, the extract is dried and concentrated and the residue is chromatographed over a silica gel column.

Yield: 1.8 g, 41% of theory.

EXAMPLE 15

1-(2-(3,4-Dimethoxyphenyl)-ethyl)-2-(pyridyl-3-carbonylaminomethyl)-5-methyl-pyrrole 1.4 g (0.011 mol) of pyridine-3-carboxylic acid and 1.8 g (0.011 mol) of carbonyldiimidazole are heated under reflux in 40 ml of tetrahydrofuran for 15 minutes. After addition of 3.0 g (0.011 mol) of 1-(2-(3,4-dimethoxyphenyl)-ethyl)-2-(aminomethyl)-5-methyl-pyrrole (compare Example 12), the mixture is stirred at room temperature for 2 hours and concentrated, aqueous sodium bicarbonate solution is added, the mixture is extracted with methylene chloride, the extract is dried and concentrated and the residue is recrystallised from isopropanol.

Yield: 1.9 g, 46% of theory; melting point: 116° to 117° C.

Analysis: Calculated: C 69.6, H 6.6, N 11.1, O 12.6; Found: C 69.8, H 6.5, N 11.0, O 12.6.

EXAMPLE 16

2-(3,4-Dimethoxy-benzoylamino-methyl)-5-methyl-pyrrole 18.1 g (0.1 mol) of 3,4-dimethoxybenzoic acid are reacted with 17.8 g (0.11 mol) of carbonyldiimidazole and 11.0 g (0.1 mol) of 2-aminomethyl-5-methyl-pyrrole (compare Example 11), as described in Example 15.

Yield: 24.4 g, 89% of theory, melting point: 125° to 126° C.

Analysis:

Calculated: C 65.7, H 6.6, N 17.5, O 10.2; Found: C 65.8, H 6.6, N 17.4, O 10.1.

EXAMPLE 17

2-(Pyridyl-3-carbonylamino-methyl)-5-methyl-pyrrole 12.9 g (0.1 mol) of pyridine-3-carboxylic acid, 17.8 g (0.11 mol) of carbonyldiimidazole and 11.0 g (0.1 mol) of 2-(aminomethyl)-5-methyl-pyrrole (compare Example 11) are reacted as described in Example 15.

Yield: 14.1 g, 66% of theory, melting point: 157° to 158° C.

Analysis: Calculated: C 67.0, H 6.1, N 19.5, O 7.4; Found: C 66.7, H 6.0, N 19.5, O 7.6.

EXAMPLE 18

2-(Acetylamino-methyl)-5-methyl-pyrrole 6.0 g (0.06 mol) of acetic anhydride in 20 ml of methylene chloride are added dropwise to 6.4 g (0.06 mol) of 2-(amino-methyl)-5-methyl-pyrrole (compare Example 11) in 20 ml of methylene chloride at 10° C. After a reaction time of 2 hours at room temperature, the mixture is concentrated and the residue is chromatographed over a silica gel column.

Yield: 5.2 g, 59% of theory.

EXAMPLE 19

1-(2-Cyanoethyl)-2-(3,4-dimethoxybenzoylamino-methyl)-5-methyl-pyrrole 3 ml of benzyltrimethyl-ammonium hydroxide (40% strength solution in methanol) are added dropwise to 5.1 g (0.019 mol) of 2-(3,4-dimethoxybenzoylamino-methyl)-5-methyl-pyrrole (compare Example 16) and 15 ml (0.23 mol) of acrylonitrile, while cooling. After 30 minutes, methylene chloride is added, the mixture is filtered, water is added, and the methylene chloride phase is separated off and concentrated. Recrystallisation from ethyl acetate gives 4.3 g of product of melting point: 175° to 176° C.

Yield: 4.3 g, 71% of theory.

Analysis: Calculated: C 66.0, H 6.5, N 12.8, O 14.7; Found: C 65.7, H 6.2, N 12.6, O 15.1.

EXAMPLE 20

1-(Aminocarbonyl-methyl)-2-(phthalimido-methyl)-5-methyl-pyrrole 5.2 g (0.02 mol) of 6-phthalimido-2,5-hexanedione, 2.3 g (0.02 mol) of glycine amide hydrochloride and 1.7 g (0.02 mol) sodium acetate are stirred in 70 ml of acetic acid at 80° C. for 3 hours and the mixture is worked up as in Example 1.

Yield: 2.3 g, 39% of theory, melting point: 169° to 171° C.

Analysis: Calculated: C 64.6, H 5.1, N 14.1, O 16.1; Found: C 64.3, H 5.2, N 14.2, O 16.3.

EXAMPLE 21

1-(3-(1-Imidazolyl)-propyl)-2-(phthalimido-methyl)-5-methyl-pyrrole hydrochloride 5.2 g (0.02 mol) of 6-phthalimido-2,5-hexanedione and 2.5 g (0.02 mol) of 3-(1-imidazolyl)-propylamine are stirred in 70 ml of acetic acid at 80° C. for 2 hours and the mixture is worked up as in Example 1. After ethanolic hydrochloric acid has been added, the product is filtered off and recrystallised from ethanol.

Yield: 1.1 g, 14% of theory, melting point: 217° to 218° C.

Analysis: Calculated: C 62.4, H 5.5, N 14.6, O 8.3; Found: C 62.3, H 5.7, N 14.9, O 8.6.

The following Examples 22 to 26 relate to the preparation of educts of the formula IIa, and Examples 27 to 38 and the Examples in Tables I to III relate to further compounds according to the invention.

EXAMPLE 22

6-Phthalimido-2,5-hexanedione bis-(dimethyl ketal)

259.3 g (1.0 mol) of 6-phthalimido-2,5-hexanedione (compare Example 2) and 318.4 g (3.0 mol) of trimethyl o-formate are heated under reflux in 320 ml of methanol and 20 ml of methanolic hydrochloric acid for 3 hour, with exclusion of moisture. After neutralisation with piperidine, the mixture is concentrated in vacuo.

Yield: 351 g (99.9% of theory), melting point: 73° to 75° C.

Calculated: C 62.8, H 6.9, N 3.9, O 26.4; Found: 62.5, 7.1, 3.9, 26.5.

EXAMPLE 23

6-Amino-2,5-hexanedione bis-(dimethyl ketal)

501.5 g (1.43 mol) of 6-phthalimido-2,5-hexanedione bis(dimethyl ketal) (compare Example 22) and 500 ml (10.3 mol) of hydrazine hydrate are heated under reflux in 6 liters of anhydrous ethanol for 15 minutes. After the phthalic acid hydrazide which has precipitated has been filtered off, the filtrate is concentrated in vacuo, the residue is taken up in methylene chloride, the mixture is dried and filtered and the filtrate is concentrated.

Yield: 250.5 g (79% of theory).

The resulting oil can be further reacted directly.

EXAMPLE 24

6-(3,4-dimethoxybenzoyl)-amino-2,5-hexanedione bis-(dimethyl ketal)

18.2 g (0.1 mol) of 3,4-dimethoxybenzoic acid and 16.2 g (0.1 mol) of carbonyldiimidazole are heated under reflux in 150 ml of anhydrous ethylene glycol dimethyl ether for 15 minutes. After the mixture has been cooled, 22.1 g (0.1 mol) of 6-amino-2,5-hexanedione bis-(dimethyl ketal) (compare Example 23) are added. After a reaction time of 2 hours at room temperature, the mixture is concentrated in vacuo, the residue is taken up in methylene chloride and the mixture is washed with sodium bicarbonate solution, dried and concentrated.

Yield: 33.7 g (87% of theory), melting point 92° to 93° C.

Calculated: C 59.2, H 8.1, N 3.6, O 29.1; Found: 59.4, 7.9, 3.4, 29.2.

EXAMPLE 25

6-Acetylamino-2,5-hexanedione bis-(dimethyl ketal)

20.6 g (0.2 mol) of acetic anhydride in 70 ml of methylene chloride are added dropwise to 44.2 g (0.2 mol) of 6-amino-2,5-hexanedione bis-(dimethyl ketal) in 70 ml of methylene chloride at 10° C. After 2 hours at 10° C., the mixture is allowed to warm to room temperature and is washed with sodium bicarbonate solution, dried and concentrated.

Yield: 50.2 g (95% of theory).

The resulting oil is further reacted directly.

EXAMPLE 26

6-(Phenyl-1-sulphenyl-2-carbonyl)-imino-2,5-hexanedione bis-(dimethyl ketal)

8.3 g (0.04 mol) of benzene-(1-sulphenic acid)-2-carboxylic acid dichloride in 17 ml of toluene are slowly added dropwise to 8.8 g (0.04 mol) of 6-amino-2,5-hexanedione bis-(dimethyl ketal) and 20 ml of triethylamine in 50 ml of toluene. After a reaction time of 3 hours, the mixture is concentrated, the residue is dissolved in methylene chloride, the solution is washed with sodium bicarbonate solution, dried and concentrated and the residue is stirred with diethyl ether.

Yield: 7.4 g (52% of theory), melting point: 115° to 116° C.

The following compounds, for example, can be prepared in an analogous manner:
- 6-(4-Methoxybenzoyl)-amino-2,5-hexanedione bis-(dimethyl ketal),
- 6-(pyridyl-3-carbonyl)-amino-2,5-hexanedione bis-(dimethyl ketal),
- 6-(4-chlorobenzoyl)-amino-2,5-hexanedione bis-(dimethyl ketal),
- 6-(1-acetyl-pyrrolidine-2-carbonyl)-amino-2,5-hexanedione bis-(dimethyl ketal),
- 6-(3,4-dichlorophenyl-1-amino-carbonyl)-amino-2,5-hexanedione bis-(dimethyl ketal),
- 6-(4-acetoxy-3-methoxy-benzoyl)-amino-2,5-hexanedione bis-(dimethyl ketal),
- 6-(4-chlorophenoxyacetyl)-amino-2,5-hexanedione bis-(dimethyl ketal),
- 6-(4-chlorophenoxyacetyl)-amino-2,5-hexanedione-bis-(ethylene glycol ketal),
- 6-(4-methylbenzoyl)-amino-2,5-hexanedione bis-(dimethyl ketal),
- 6-(2-methoxycarbonylphenyl-1-sulphonyl)-amino-2,5-hexanedione bis-(dimethyl ketal),
- 6-(3-acetoxy-2-phenyl-propionyl)-amino-2,5-hexanedione bis-(dimethyl ketal),
- 6-(2-acetoxy-2-phenyl-acetyl)-amino-2,5-hexanedione bis-(dimethyl ketal),
- 6-(4-nitrobenzoyl)-amino-2,5-hexanedione bis-(dimethyl ketal),
- 6-(4-aminobenzoyl)-amino-2,5-hexanedione bis-(dimethyl ketal), 6-(4-methylphenyl-1-sulphonyl)-amino-2,5-hexanedione bis-(dimethyl ketal),
6-(3-hydroxy-2-phenyl-propionyl)-amino-2,5-hexanedione bis-(dimethyl ketal),
6-(2-hydroxy-2-phenyl-acetyl)-amino-2,5-hexanedione bis-(dimethyl ketal),
6-(1-formyl-pyrrolidone-3-carbonyl)-amino-2,5-hexanedione bis-(dimethyl ketal),
7-phthalimido-3,6-heptanedione bis-(dimethyl ketal),
5-phthalimido-1-phenyl-1,4-pentane-dione bis-(dimethyl ketal),
7-phthalimido-2,5-hexanedione bis-(dimethyl ketal),
8-phthalimido-2,5-octanedione bis-(dimethyl ketal),
6-succinimido-2,5-hexanedione bis-(ethylene glycol ketal),
6-maleimido-2,5-hexanedione bis-(ethylene glycol ketal),
6-(thiophene-2-carbonyl)-amino-2,5-hexanedione bis-(dimethyl ketal),
6-(phenylene-2,3-dicarbonyl)-imino-2,5-hexanedione bis-(dimethyl ketal),
6-(phenylene-2-carbonyl-1-sulphonyl)-imino-2,5-hexanedione bis-(dimethyl ketal) and
6-(phenylene-2-carbonyl-1-sulphinyl)-imino-2,5-hexanedione bis-(dimethyl ketal). The resulting compounds can in most cases be further processed in the form of the crude products.

EXAMPLE 27

1-(2-Acetylamino-ethyl)-2-(4-methoxybenzoyl)-aminomethyl-5-methyl-pyrrole 32 g (0.09 mol) of 6-(4-methoxybenzoyl)-amino-2,5-hexanedione bis-(dimethyl ketal) and 9.7 g (0.095 mol) of 1-acetylamino-ethylenediamine are stirred in 200 ml of acetic acid at 40° C. for 12 hours. After the mixture has been concentrated in vacuo, the residue is taken up in methylene chloride, the mixture is washed with sodium bicarbonate solution, dried and concentrated and the residue is stirred with diethyl ether.

Yield: 7.4 g (25% of theory), melting point 150° to 151° C.

Calculated: C 65.6, H 7.0, N 12.8, O 14.6; Found: 65.7, 7.0, 12.5, 14.5.

EXAMPLE 28

1-(Methoxycarbonyl-methyl)-2-(phthalimido-methyl)-5-phenylpyrrole 9.6 g (0.03 mol) of 5-phthalimido-1-phenyl-1,4-pentanedione, 5.0 g (0.04 mol) of glycine methyl ester hydrochloride and 3.2 g (0.04 mol) of anhydrous sodium acetate are stirred in 80 ml of propionic acid at 60° C. for 20 hours. Purification is by column chromatography. Solid phase: "Silica-Woelm", particle size 0.1 to 0.2 mm; manufacturer: Messrs. Woelm, Eschwege, Germany; mobile phase: methylene chloride.

Yield: 3.9 g (35% of theory), melting point 160° to 162° C.

Calculated: C 70.6, H 4.8, N 7.5, O 17.1; Found: 70.4, 5.0, 7.5, 17.2.

EXAMPLE 29

1-(2-(3-Indolyl)-1-methoxycarbonyl)-ethyl-2-(phthalimido-methyl)-5-methyl-pyrrole 3.9 g (0.015 mol) of 6-phthalimido-2,5-hexanedione, 4.0 g (0.016 mol) of tryptophan methyl ester hydrochloride and 2 ml (0.014 mol) of triethylamine are stirred in 80 ml of ethylene glycol monomethyl ether at 50° C. for 6 hours and the mixture is worked up as in Example 27.

Yield: 3.5 g (53% of theory), melting point 168° to 169° C.

Calculated: C 70.7, H 5.3, N 9.5, O 14.5; Found: 71.0, 5.2, 9.4, 14.7.

EXAMPLE 30

1-(4,5-Dimethoxy-1-methoxycarbonyl-phenyl)-2-(4-chlorophenoxyacetyl-amino-methyl)-5-methyl-pyrrole 9.7 g (0.025 mol) of 6-(4-chlorophenoxyacetyl)-amino-2,5-hexanedione bis-(dimethyl ketal) and 5.3 g of 4,5-dimethoxyanthranilic acid are stirred in 100 ml of acetic acid at 50° C. for 8 hours and the mixture is worked up as in Example 27.

Yield: 2.2 g (19% of theory), melting point 92° to 93° C.

Calculated: C 61.0, H 5.3, Cl 7.5, N 5.9, O 20.3; Found: 60.5, 5.4, 7.8, 5.8, 20.4.

EXAMPLE 31

1-(Methoxycarbonyl-methyl)-2-(2-phthalimido-ethyl)-5-methyl-pyrrole 82 g (0.03 mol) of 7-phthalimido-2,5-heptanedione, 5.0 g (0.04 mol) of glycine methyl ester hydrochloride and 3.3 g (0.04 mol) of sodium acetate are stirred in 150 ml of formic acid at 60° C. for 4 hours and the mixture is worked up as in Example 27.

Yield: 2.9 g (30% of theory), melting point 125° to 128° C.

Calculated: C 66.2, H 5.6, N 8.6, O 19.6; Found: 66.0, 5.6, 9.0, 19.2.

EXAMPLE 32

1-(2-(Ethoxycarbonyl)-ethyl)-2-(phthalimido-methyl)-5-methyl-pyrrole 3.9 g (0.015 mol) of 6-phthalimido-2,5-hexanedione, 3.1 g (0.02 mol) of β-alanine ethyl ester hydrochloride and 3 ml (0.02 mol) of triethylamine are stirred in 80 ml of glacial acetic acid at 50° C. for 8 hours and the mixture is worked up as in Example 27.

Yield: 2.1 g (41% of theory), melting point 106° to 108° C.

Calculated: C 67.0, H 5.9, N 8.2, O 18.8; Found: 67.3, 5.9, 8.5, 18.7.

EXAMPLE 33

1-(3-(Ethoxycarbonyl)-propyl)-2-(phthalimido-methyl)-5-methyl-pyrrole 3.9 g (0.015 mol) of 6-phthalimido-2,5-hexanedione, 2.5 g ((0.015 mol) of ethyl 4-aminobutyrate hydrochloride and 1.3 g (0.015 mol) of sodium acetate are stirred in 50 ml of toluene at 60° C. for 23 hours. After the mixture has been concentrated, it is worked up as in Example 22.

Yield: 2.7 g (51% of theory), melting point 92° to 94° C.

Calculated: C 67.8, H 6.3, N 7.9, O 18.1; Found: 67.2, 6.3, 8.1, 17.1.

EXAMPLE 34

1-(Methoxycarbonyl-methyl)-2-(phthalimido-methyl)-5-ethylpyrrole 6.8 g (0.025 mol) of 7-phthalimido-3,6-heptanedione, 3.5 g (0.028 mol) of glycine methyl ester hydrochloride and 2.3 g (0.028 mol) of sodium acetate are stirred in 150 ml of cyclohexanol at 60° C. for 13 hours and the mixture is worked up as in Example 22.

Yield: 5.4 g (66% of theory), melting point 94° to 95° C.

Calculated: C 66.2, H 5.6, N 8.6, O 19.6; Found: 66.3, 5.6, 8.8, 19.7.

EXAMPLE 35

1-(2-Methoxy-carbonyl-4,5,6-trimethoxy-phenyl)-2-(phthalimidomethyl)-5-methyl-pyrrole 7.8 g (0.03 mol) of 6-phthalimido-2,5-hexanedione and 7.3 g (0.03 mol) of methyl 2-amino-3,4,5-trimethoxybenzoate are stirred in 120 ml of dimethylformamide at 80° C. for 16 hours and the mixture is worked up as in Example 27.

Yield: 3.5 g (25% of theory), melting point 146° to 148° C.

Calculated: C 64.6, H 5.2, N 6.0, O 24.1; Found: 64.0, 5.3, 6.3, 24.3.

EXAMPLE 36

1-(Hydroxy-carbonyl-methyl)-2-(phthalimido-methyl)-5-methyl-pyrrole 5.2 g (0.02 mol) of 6-phthalimido-2,5-hexanedione and 1.6 g (0.02 mol) of glycine are stirred in 50 ml of acetonitrile at 80° C. for 1 hour. After the mixture has been concentrated, it is extracted under alkaline conditions with methylene chloride and the extract is acidified and extracted again. The resulting product is recrystallised from methanol.

Yield: 2.8 g (47% of theory), melting point 154° to 157° C.

Calculated: C 64.4, H 4.7, N 9.4, O 21.5; Found: 64.3, 5.1, 9.2, 21.3.

EXAMPLE 37

1-Cyanomethyl-2-(phthalimido-methyl)-5-methyl-pyrrole 10.4 g (0.04 mol) of 6-phthalimido-2,5-hexanedione, 6.2 g (0.04 mol) of aminoacetonitrile sulphate and 6.8 g (0.08 mol) of sodium acetate are stirred in 200 ml of ethylene glycol dimethyl ether at 80° C. for 16 hours and the mixture is worked up as in Example 27.

Yield: 5.2 g (47% of theory), melting point 166° to 168° C.

Calculated: C 68.8, H 4.7, N 15.0, O 11.5; Found: 68.1, 5.0, 14.8, 11.9.

EXAMPLE 38

1-(tert.-Butoxy-carbonyl-methyl)-2-(phthalimido-methyl)-5-methyl-pyrrole 13.0 g (0.05 mol) of 6-phthalimido-2,5-hexanedione and 6.6 g (0.05 mol) of glycine tert.-butyl ester are stirred in 250 ml of tetrahydrofuran at 80° C. for 20 hours and the mixture is worked up as in Example 27.

Yield: 8.7 g (49% of theory), melting point 134° to 135° C.

Calculated: C 67.8, H 6.3, N 7.9, O 18.1; Found: 68.1, 6.3, 7.6, 18.3.

Further examples of compounds prepared are given in the following Tables I to III.

TABLE I

Compounds of the formula I where R = $CH_3$, $R^2$ = H and n = 1, and

| $R^1$ | $R^3$ | melting point: (°C.) |
|---|---|---|
| —$CH_2COOCH_3$ | 3,4-dimethoxy-benzoyl | 138–139 |
| —$CH_2CH_2COOC_2H_5$ | 3,4-dimethoxy-benzoyl | 147–148 |
| —$CH_2CH_2CH_2COOC_2H_5$ | 3,4-dimethoxy-benzoyl | 96–98 |
| —$CH_2CONH_2$ | 3,4-dimethoxy-benzoyl | 215–217 |
| —$CH_2CH_2NHCOCH_3$ | 3,4-dimethoxy-benzoyl | 142–143 |
| —$CH_2COOCH_3$ | nicotinoyl | 117–119 |
| 2-(methoxycarbonyl)-4,5-dimethoxy-phenyl | nicotinoyl | 121–123 |
| —$CH_2COOCH_3$ | $CH_3CO$— | 114–116 |
| —$CH_2COOCH_3$ | 4-methoxy-benzoyl | 104–105 |
| —$CH(CH_3)COOC_2H_5$ | 4-chloro-benzoyl | 116–118 |
| —$CH_2COOCH_3$ | 4-chloro-benzoyl | 121–123 |
| —$CH_2COOCH_3$ | 4-nitro-benzoyl | 164–166 |
| —$CH_2COOCH_3$ | 3-methoxy-4-acetoxy-benzoyl | 120–122 |
| —$CH_2COOCH_3$ | N—acetyl-2-pyrrolidinyl-carbonyl | 126–127 |
| —$CH_2COOCH_3$ | 4-chlorophenoxy-acetyl | 91–92 |

TABLE II

Compounds of the formula I where R = $CH_3$, n = 1 and

| $R^1$ | $R^2$ and $R^3$ together | melting point: (°C.) |
|---|---|---|
| 2-methoxy-carbonyl-4,5,6-trimethoxy-phenyl | phthaloyl | 146–148 |
| —$CH_2COOCH_3$ | pyridine-2,3-dicarbonyl | 153–155 |
| —$CH_2COOCH_3$ | benzene-1-sulphonyl-2-carbonyl | 126–127 |
| 2-(3,4-dimethoxy-phenyl-ethyl | phthaloyl | 112–113 |

TABLE III

Compounds of the formula I where R = H, $R^1$ = $CH_3$, n = 2 and

| $R^2$ | $R^3$ | melting point: (°C.) |
|---|---|---|
| H | phthaloyl | 139–141 |
| | 3,4-dimethoxy-benzoyl | 117–119 |

Pharmaceutical products are described in the following examples:

EXAMPLE 39

Tablets can be prepared according to the following formulation:

| Active compound | 2 mg |
|---|---|
| Lactose | 60 mg |
| Maize starch | 30 mg |
| Soluble starch | 4 mg |
| Magnesium stearate | 4 mg |
| | 100 mg |

EXAMPLE 40

The following composition is suitable for the preparation of soft gelatin capsules containing 5 mg of active compound per capsule:

| Active compound | 5 mg |
|---|---|
| Mixture of triglycerides of coconut oil | 150 mg |
| Capsule contents | 155 mg |

EXAMPLE 41

The following formulation is suitable for the preparation of coated tablets:

| | |
|---|---|
| Active compound | 1 mg |
| Maize starch | 100 mg |
| Lactose | 60 mg |
| Secondary calcium phosphate | 30 mg |
| Soluble starch | 3 mg |
| Magnesium stearate | 2 mg |
| colloidal silicic acid | 4 mg |
| | 200 mg |

EXAMPLE 42

Injection solutions containing 1 mg of active compound per ml can be prepared according to the following recipe:

| | |
|---|---|
| Active compound | 1.0 mg |
| Polyethylene glycol 400 | 0.3 mg |
| Sodium chloride | 2.7 mg |
| Water for injection purposes to | 1 ml |

EXAMPLE 43

Emulsions containing 3 mg of active compound per 5 ml can be prepared according to the following recipe:

| | |
|---|---|
| Active compound | 0.06 mg |
| Neutral oil | q.s. |
| Sodium carboxymethylcellulose | 0.6 g |
| Polyoxyethylene stearate | q.s. |
| Pure glycerol | 0.2 to 2 g |
| Aroma substances | q.s. |
| Water (demineralised or distilled) to | 100 ml |

EXAMPLE 44

Coated tablets containing an active compound according to the invention and another therapeutically active substance:

| | |
|---|---|
| Active compound | 6 mg |
| Propranolol | 40 mg |
| Lactose | 90 mg |
| Maize starch | 90 mg |
| Secondary calcium phosphate | 34 mg |
| Soluble starch | 3 mg |
| Magnesium stearate | 3 mg |
| colloidal silicic acid | 4 mg |
| | 270 mg |

EXAMPLE 45

Coated tablets containing an active compound according to the invention and another therapeutically active substance:

| | |
|---|---|
| Active compound | 5 mg |
| Molsidomine | 5 mg |
| Lactose | 60 mg |
| Maize starch | 90 mg |
| Secondary calcium phosphate | 30 mg |
| Soluble starch | 3 mg |
| Magnesium stearate | 3 mg |
| Colloidal silicic acid | 4 mg |
| | 200 mg |

EXAMPLE 46

Capsules containing an active compound according to the invention and another therapeutically active substance:

| | |
|---|---|
| Active compound | 5 mg |
| Prazosin | 5 mg |
| Maize starch | 185 mg |
| | 195 mg |

The following results were obtained during pharmacological testing.

1. "Nitrite hypoxia"

In this test, cerebral hypoxia is produced in mice with $NaNO_2$ (250 mg/kg subcutaneously) in accordance with the method of Gibsen and Bless (J. Neurochem. 27, 1976), this hypoxia ending with the death of the experimental animals. It is ascertained whether the survival time is influenced by premedication with the test substance. The results are shown in Tables IV to VII.

TABLE IV

Percentage increase in the survival time on administration of 250 mg/kg of $NaNO_2$ subcutaneously and premedication with compounds of the formula I where $R^2$ and $R^3$ together are phthaloyl and

| R | $R^1$ | n | Percentage increase |
|---|---|---|---|
| —$CH_3$ | —H | 1 | 17.2 |
| —$C_2H_5$ | —$CH_2COOCH_3$ | 1 | 13.3 |
| —$CH_3$ | —$CH_2COOCH_3$ | 1 | 42 |
| —$CH_3$ | —$CH_2COOC_2H_5$ | 1 | 11 |
| —$CH_3$ | —$CH_2CN$ | 1 | 9 |
| —$CH_3$ | —$CH_2CH_2NHCOCH_3$ | 1 | 30 |
| —$CH_3$ | —$CH_2CO—C(CH_3)_3$ | 1 | 24 |
| —$CH_3$ | —$C_6H_4$—2-COO—$CH_3$ | 1 | 3.6 |
| —$CH_3$ | —$CH_2CH_2C_6H_3$—3,4-(O—$CH_3)_2$ | 1 | |
| —$CH_3$ | 2-methoxycarbonyl-4,5-dimethoxy-phenyl | 1 | 31 |
| —$CH_3$ | 2-(4- or -5-imidazolyl)-ethyl | 1 | 22 |
| —$CH_3$ | —$CH_2CONH_2$ | 1 | 34 |
| —H | —$CH_3$ | 2 | 21 |
| —$C_6H_5$ | —$CH_2COOCH_3$ | 1 | 25 |
| —$CH_3$ | —$CH_2COOCH_3$ | 2 | 15 |
| —$CH_3$ | 2-(methoxy-carbonyl)-4,5,6-trimethoxy-phenyl | 1 | 14 |
| —$CH_3$ | —$CH_2CH_2N(CH_3)_2$ | 1 | 28 |

TABLE V

Percentage increase in the survival time on administration of 250 mg/kg of $NaNO_2$ subcutaneously and premedication with compounds of the formula I where $R^2$ = H and $R^3$ = 3,4-dimethoxy-benzoyl and

| R | $R^1$ | n | Percentage increase |
|---|---|---|---|
| —$CH_3$ | —$CH_2CH_2NHCOCH_3$ | 1 | 24.2 |
| —$CH_3$ | —$CH_2COOCH_3$ | 1 | 1.6 |
| —$CH_3$ | —$CH_2CONH_2$ | 1 | 28.7 |
| —$CH_3$ | —$CH_2CH_2COOC_2H_5$ | 1 | 4.8 |
| —H | —$CH_3$ | 2 | 12 |
| —$CH_3$ | —$CH_2CH_2CH_2COOC_2H_5$ | 1 | 21.8 |

TABLE VI

Percentage increase in the survival time on administration of 250 mg/kg of NaNO$_2$ subcutaneously and premedication with compounds of the formula I where R = CH$_3$, R$^2$ = H and n = 1 and

| R$^1$ | R$^3$ | Percentage increase |
|---|---|---|
| —CH$_2$COOCH$_3$ | 4-Cl—C$_6$H$_4$—CO— | 2 |
| —CH$_2$COOCH$_3$ | 4-Cl—C$_6$H$_4$—OCH$_2$CO— | 2.7 |
| 2-(methoxy-carbonyl)-4,5-dimethoxy-phenyl | 4-Cl—C$_6$H$_4$—OCH$_2$CO— | 34.9 |
| —CH$_2$COOCH$_3$ | CH$_3$CO— | 9 |
| —CH$_2$COOCH$_3$ | 4-NO$_2$C$_6$H$_4$—CO— | 7 |
| —CH$_2$CH$_2$NHCOCH$_3$ | 4-CH$_3$O—C$_6$H$_4$—CO— | 8 |
| —CH$_2$COOCH$_3$ | 4-CH$_3$O—C$_6$H$_4$—CO— | 2 |
| —CH$_2$COOCH$_3$ | 4-acetoxy-3-methoxy-benzoyl | 6.4 |
| —H | nicotinoyl | 16.9 |
| —CH$_2$CH$_2$—C$_6$H$_3$—3,4-(OCH$_3$)$_2$ | nicotinoyl | 12 |
| —CH(CH$_3$)COOC$_2$H$_5$ | 4-Cl—C$_6$H$_4$—CO— | 30 |

TABLE VII

Percentage increase in the survival time on administration of 250 mg/kg of NaNO$_2$ subcutaneously and premedication with compounds of the formula I where R = CH$_3$ and n = 1 and

| R$^1$ | R$^2$ and R$^3$ together | Percentage increase |
|---|---|---|
| —CH$_2$COOCH$_3$ | pyridine-2,3-dicarbonyl | 7.8 |
| —CH$_2$COOCH$_3$ | phenylene-1-carbonyl-2-sulphenyl | 11.3 |

2. "Passive avoidance"

The test apparatus is a light/dark box with an electrifiable grid floor in the dark part.

90 minutes after administration of the control injection and product injection, unexperienced male mice are treated with scopolamine hydrobromide (mg/kg subcutaneously). 5 minutes later, the mice are placed in the light part of the box. After being transferred to the dark part of the box, they receive an unpleasant electric shock in the feet. After 24 hours, each mouse is placed once in the light part of the test apparatus and the residence time (maximum of 180 seconds) is measured. The animals treated with an active dose of a product and scopolamine have a long residence time, as do the animals which have not been treated with scopolamine, whilst those treated with a control injection and scopolamine show a short residence time. The results are given in Tables VIII to XI.

TABLE VIII

Percentage decrease in scopolamine-induced amnesia, recognisable by an increase in the time until the animal enters the dark part of the passive avoidance test chamber
Compounds of the formula I, where R$^2$ and R$^3$ together are phthaloyl and

| R | R$^1$ | n | Percentage decrease |
|---|---|---|---|
| —CH$_3$ | —CH$_2$CONH$_2$ | 1 | 67 |
| —CH$_3$ | —CH$_2$COOCH$_3$ | 1 | 178 |
| —CH$_3$ | —CH$_2$COOCH$_3$ | 2 | 52 |
| —CH$_3$ | —H | 1 | 10 |
| —CH$_3$ | —CH$_2$CH$_2$CH$_2$COOC$_2$H$_5$ | 1 | 117 |
| —CH$_3$ | —CH$_2$CN | 1 | 126 |
| —CH$_3$ | —CH$_2$COOC$_2$H$_5$ | 1 | 111 |
| —CH$_3$ | —CH$_2$CH$_2$NHCOCH$_3$ | 1 | 167 |
| —CH$_3$ | —CH$_2$CH$_2$N(CH$_3$)$_2$ | 1 | 91 |
| —CH$_3$ | 2-methoxy-carbonyl-4,5-dimethoxy-phenyl | 1 | 95 |
| —CH$_3$ | —CH$_2$CH$_2$—C$_6$H$_3$—3,4-(OCH$_3$)$_2$ | 1 | 115 |
| —CH$_3$ | —C$_6$H$_4$—2-(CO—OCH$_3$) | 1 | 63 |
| —CH$_3$ | —CH$_2$CO—C(CH$_3$)$_3$ | 1 | 29 |
| —C$_6$H$_5$ | —CH$_2$COOCH$_3$ | 1 | 32 |

TABLE VIII-continued

Percentage decrease in scopolamine-induced amnesia, recognisable by an increase in the time until the animal enters the dark part of the passive avoidance test chamber
Compounds of the formula I, where R$^2$ and R$^3$ together are phthaloyl and

| R | R$^1$ | n | Percentage decrease |
|---|---|---|---|
| —C$_2$H$_5$ | —CH$_2$COOCH$_3$ | 1 | 69 |
| —H | —CH$_3$ | 2 | 59 |

TABLE IX

Percentage decrease in scopolamine-induced amnesia, recognisable by an increase in the time until the animal enters the dark part of the passive avoidance test chamber
Compounds of the formula I where R$^2$ = H and R$^3$ = 2,3-dimethoxybenzoyl and

| R | R$^1$ | n | Percentage decrease |
|---|---|---|---|
| —CH$_3$ | —CH$_2$CONH$_2$ | 1 | 49 |
| —CH$_3$ | —CH$_2$CH$_2$NHCOCH$_3$ | 1 | 42 |
| —CH$_3$ | —H | 1 | 87 |
| —CH$_3$ | —CH$_2$COOCH$_3$ | 1 | 23 |
| —CH$_3$ | —CH$_2$CH$_2$COOC$_2$H$_5$ | 1 | 7 |
| —H | —CH$_3$ | 2 | 64 |

TABLE X

Percentage decrease in scopolamine-induced amnesia, recognisable by an increase in the time until the animal enters the dark part of the passive avoidance test chamber
Compounds of the formula I where R = CH$_3$, R$^2$ = H and n = 1 and

| R$^1$ | R$^3$ | Percentage decrease |
|---|---|---|
| 2-methoxycarbonyl-4,5-dimethoxy-phenyl | 4-Cl—C$_6$H$_4$—OCH$_2$CO— | 91 |
| —CH$_2$COOCH$_3$ | CH$_3$CO— | 24 |
| —CH$_2$COOCH$_3$ | 4-CH$_3$O—C$_6$H$_4$—CO— | 20 |
| —CH$_2$COOCH$_3$ | 4-Cl—C$_6$H$_4$—CO— | 55 |
| —H | nicotinoyl | 9 |
| —CH$_2$CH$_2$—C$_6$H$_3$—3,4-(OCH$_3$)$_2$ | nicotinoyl | 62 |

TABLE XI

Percentage decrease in scopolamine-induced amnesia, recognisable by an increase in the time until the animal enters the dark part of the passive avoidance test chamber
Compounds of the formula I where R = CH$_3$ and n = 1 and

| R$^1$ | R$^2$ and R$^3$ together | Percentage decrease |
|---|---|---|
| —CH$_2$COOCH$_3$ | pyridine-2,3-dicarbonyl | 31 |
| —CH$_2$COOCH$_3$ | phenylene-1-carbonyl-2-sulphenyl | 35 |

What is claimed is:

1. Method for the treatment of humans for combating and preventing disorders which are caused by a restriction in cerebral function, and for the treatment of cerebral aging processes, which comprises administering to a human subject to or afflicted with such disorders and for aging processes an effective dose of 2-(aminoalkyl)-pyrrole derivative of the formula I

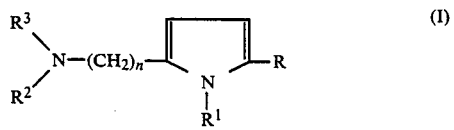

wherein
R denotes hydrogen, alkyl($C_1$-$C_5$) or phenyl;
$R^1$ denotes hydrogen, alkyl($C_1$-$C_5$), cyano-alkyl(-$C_1$-$C_4$), alkoxy($C_1$-$C_4$)-carbonyl, alkoxy($C_1$-$C_4$)-carbonyl-alkyl($C_1$-$C_4$); $R^7(R^8)$N-carbonylalkyl(-$C_1$-$C_4$), acetyl-amino-ethyl, phenyl or phenyl-alkyl($C_1$-$C_4$), it being possible for the phenyl or the phenyl of the phenyl-alkyl also to be monosubstituted or polysubstituted by halogen, alkoxy($C_1$-$C_4$), alkyl($C_1$-$C_4$), $R^4(R^5)$N-, hydroxyl, mercapto, alkylmercapto($C_1$-$C_4$), nitro, cyano, alkoxy($C_1$-$C_4$)-carbonyl or alkoxy($C_1$-$C_4$)-carbonyl-alkyl($C_1$-$C_4$) or $R^1$ denotes $R^4(R^5)$N-$R^6$-, hydroxy-carbonyl-alkyl($C_1$-$C_4$), 1-(alkoxy($C_1$-$C_4$)-carbonyl)-2-mercapto-ethyl, 1-(alkoxy($C_1$-$C_4$)-carbonyl)-2-hydroxy-ethyl, 1-(alkoxy($C_1$-$C_4$)-carbonyl)-2-alkoxy($C_1$-$C_4$)-ethyl, 1-(alkoxy($C_1$-$C_4$)-carbonyl-2-alkylthio($C_1$-$C_4$)-ethyl, 1-(alkoxy($C_1$-$C_4$)-carbonyl)-2-(alkyl($C_1$-$C_4$)-carbonyl-thio)-ethyl, 1-(alkoxy($C_1$-$C_4$)-carbonyl)-2-(alkyl($C_1$-$C_4$)-carbonyl-oxy)-ethyl, or 1-(alkoxy($C_1$-$C_4$)-carbonyl)-2-phenyl-ethyl;
$R^2$ und $R^3$ independently of one another denote hydrogen, alkyl($C_1$-$C_5$), alkanoyl($C_1$-$C_5$), alkanoyl(-$C_2$-$C_5$) which is mono-, di- or tri-substituted by amino, alkoxy($C_1$-$C_4$), hydroxyl, alkanoyloxy($C_1$-$C_4$), phenyl or halogen, phenylcarbonyl, phenylcarbonyl which is mono- or polysubstituted by halogen, alkoxy($C_1$-$C_4$), alkyl($C_1$-$C_4$), amino, $R^4(R^5)$N-, hydroxy, alkanoyloxy($C_1$-$C_4$), mercapto, alkylmercapto($C_1$-$C_4$), nitro, cyano, alkoxy($C_1$-$C_4$)-carbonyl or aminosulphonyl, or $R^2$ and/or $R^3$ denote cycloalkylcarbonyl with 5 to 7 C atoms in the cycloalkyl radical or (4-chlorophenoxy)-acetyl;
$R^4$ and $R^5$ denote hydrogen or alkyl($C_1$-$C_4$);
$R^6$ denotes alkylene($C_1$-$C_4$);
$R^7$ and $R^8$ independently of one another denote hydrogen or alkyl($C_1$-$C_4$);
and n denotes 1, 2 or 3, or a pharmacologically acceptable acid addition salt thereof.

2. Method according to claim 1, wherein a derivative of formula I is administered in which R denotes methyl.

3. Method according to claim 1, wherein a derivative of formula I is administered in which $R^3$ denotes hydrogen, 3,4-dimethoxybenzoyl, 4-chlorobenzoyl, 4-chlorophenoxyacetyl or acetyl.

4. Method according to claim 1, wherein a derivative of formula I is administered in which $R^1$ denotes hydrogen, 2-dimethylaminoethyl, 3,4-dimethoxyphenyl-ethyl, 4,5-dimethoxy-2-(methoxycarbonyl)-phenyl, methoxycarbonylmethyl, acetylamino-ethyl, cyanoethyl, 2-methoxy-carbonyl-phenyl, 2-methoxy-carbonyl-, 4,5,6-trimethoxy-phenyl or aminocarbonylmethyl.

5. Method according to claim 1, wherein 5-Methyl-2-(3,4-dimethoxybenzoyl-amino-methyl)-pyrrole is administered.

6. Method according to claim 1, wherein 1-(2-Methoxycarbonyl-4,5-dimethoxy-phenyl)-5-methyl-2-(4-chlorophenoxy-acetylamino-methyl)-pyrrole is administered.

7. Pharmaceutical product useful for the treatment of humans for combating and preventing disorders which are caused by a restriction in cerebral function, and for the treatment of cerebral aging processes, said product comprising an effective amount of a pharmacologically-active compound and a physiologically-acceptable, pharmacologically-inert excipient, said active compound comprising a 2-(aminoalkyl)-pyrrole derivative of the formula I

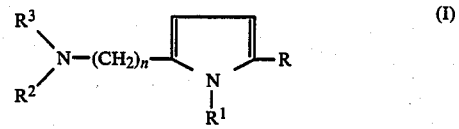

wherein
R denotes hydrogen, alkyl($C_1$-$C_5$) or phenyl;
$R^1$ denotes hydrogen, alkyl($C_1$-$C_5$), cyano-alkyl(-$C_1$-$C_4$), alkoxy($C_1$-$C_4$)-carbonyl, alkoxy($C_1$-$C_4$)-carbonyl-alkyl($C_1$-$C_4$); $R^7(R^8)$N-carbonylalkyl(-$C_1$-$C_4$), acetyl-amino-ethyl, phenyl or phenyl-alkyl($C_1$-$C_4$), it being possible for the phenyl or the phenyl of the phenyl-alkyl also to be monosubstituted or polysubstituted by halogen, alkoxy($C_1$-$C_4$), alkyl($C_1$-$C_4$), $R^4(R^5)$N-, hydroxyl, mercapto, alkylmercapto($C_1$-$C_4$), nitro, cyano, alkoxy($C_1$-$C_4$)-carbonyl or alkoxy($C_1$-$C_4$)-carbonyl-alkyl($C_1$-$C_4$) or $R^1$ denotes $R^4(R^5)$N-$R^6$-, hydroxy-carbonyl-alkyl($C_1$-$C_4$), 1-(alkoxy($C_1$-$C_4$)-carbonyl)-2-mercapto-ethyl, 1-(alkoxy($C_1$-$C_4$)-carbonyl)-2-hydroxy-ethyl, 1-(alkoxy($C_1$-$C_4$)-carbonyl)-2-alkoxy($C_1$-$C_4$)-ethyl, 1(alkoxy($C_1$-$C_4$)-carbony-2-alkylthio($C_1$-$C_4$)-ethyl, 1-(alkoxy($C_1$-$C_4$)-carbonyl)-2-(alkyl($C_1$-$C_4$)-carbonyl-thio)-ethyl, 1(alkoxy($C_1$-$C_4$)-carbonyl)-2-(alkyl($C_1$-$C_4$)-carbonyl-oxy)-ethyl, or 1-(alkoxy($C_1$-$C_4$)-carbonyl)-2-phenyl-ethyl;
$R^2$ und $R^3$ independently of one another denote hydrogen, alkyl($C_1$-$C_5$), alkanoyl($C_1$-$C_5$), alkanoyl(-$C_2$-$C_5$) which is mono-, di- or tri-substituted by amino, alkoxy($C_1$-$C_4$), hydroxyl, alkanoyloxy($C_1$-$C_4$), phenyl or halogen, phenylcarbonyl, phenylcarbonyl which is mono- or polysubstituted by halogen, alkoxy($C_1$-$C_4$), alkyl($C_1$-$C_4$), amino, $R^4(R^5)$N-, hydroxy, alkanoyloxy($C_1$-$C_4$), mercapto, alkylmercapto($C_1$-$C_4$), nitro, cyano, alkoxy($C_1$-$C_4$)-carbonyl or aminosulphonyl, or $R^2$ and/or $R^3$ denote cycloalkylcarbonyl with 5 to 7 C atoms in the cycloalkyl radical or (4-chlorophenoxy)-acetyl;
$R^4$ and $R^5$ denote hydrogen or alkyl($C_1$-$C_4$);
$R^6$ denotes alkylene($C_1$-$C_4$);
$R^7$ and $R^8$ independently of one another denote hydrogen or alkyl($C_1$-$C_4$);
and n denotes 1, 2 or 3, or a pharmaceutically acceptable acid addition salt thereof.

8. Pharmaceutical product according to claim 7, wherein R of the active compound is methyl.

9. Pharmaceutical product according to claim 7, wherein $R^3$ of the active compound denotes hydrogen, 3,4-dimethoxybenzoy, 4-chlorobenzoy, 4-chlorophenoxyacetyl or acetyl.

10. Pharmaceutical product according to claim 7, wherein $R^1$ of the active compound denotes hydrogen, 2-dimethylaminoethyl, 3,4-dimethoxyphenyl-ethyl, 4,5-dimethoxy-2-(methoxycarbonyl)-phenyl, methoxycarbonylmethyl, acetylamino-ethyl, cyanoethyl, 2-methoxy-carbonyl-phenyl, 2-methoxy-carbonyl-, 4,5,6-trimethoxy-phenyl or aminocarbonylmethyl.

11. Pharmaceutical product according to claim 7, wherein the active compound is 5-Methyl-2-(3,4-dimethoxybenzoylamino-methyl)-pyrrole.

12. Pharmaceutical product according to claim 7, wherein the active compound is 1-(2-Methoxy-carbonyl-4,5-dimethoxy-phenyl)-5-methyl-2-(4-chlorophenoxy-acetylaminomethyl)-pyrrole.

* * * * *